(12) United States Patent
Hauger et al.

(10) Patent No.: US 12,153,220 B2
(45) Date of Patent: Nov. 26, 2024

(54) HEAD-MOUNTED VISUALIZATION SYSTEM

(71) Applicant: Carl Zeiss Meditec AG, Jena (DE)

(72) Inventors: Christoph Hauger, Aalen (DE);
Christoph Schaeff, Aalen (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/909,265

(22) PCT Filed: Feb. 26, 2021

(86) PCT No.: PCT/EP2021/054900
§ 371 (c)(1),
(2) Date: Sep. 2, 2022

(87) PCT Pub. No.: WO2021/175727
PCT Pub. Date: Sep. 10, 2021

(65) Prior Publication Data
US 2023/0087402 A1    Mar. 23, 2023

(30) Foreign Application Priority Data
Mar. 2, 2020   (DE) ............ 10 2020 202 624.6
Nov. 24, 2020  (DE) ............ 10 2020 131 029.3

(51) Int. Cl.
*G02B 27/01*    (2006.01)
*A61B 90/00*    (2016.01)
(Continued)

(52) U.S. Cl.
CPC ......... *G02B 27/0172* (2013.01); *A61B 90/37* (2016.02); *G02B 5/30* (2013.01);
(Continued)

(58) Field of Classification Search
CPC .. G02B 27/0172; G02B 5/30; G02B 27/0179; G02B 30/25; G02B 27/283;
(Continued)

(56) References Cited

U.S. PATENT DOCUMENTS 6,559,813 B1   5/2003  DeLuca et al.
6,683,726 B2   1/2004  Endo et al.
(Continued)

FOREIGN PATENT DOCUMENTS

CN    1756986 A    4/2006
CN  102483566 A    5/2012
(Continued)

OTHER PUBLICATIONS

International Preliminary Report on Patentability, WIPO Application No. PCT/EP2021/055034, mailed Jul. 4, 2022.
(Continued)

*Primary Examiner* — Thanh Luu
*Assistant Examiner* — Mai Thi Ngoc Tran
(74) *Attorney, Agent, or Firm* — Alston & Bird LLP

(57) ABSTRACT

The invention relates to a head-mounted visualization system having a wearing system, at least one light-transmissive optical system, an image generation device designed to generate image information based on the image data supplied to the image generation device, wherein the optical system is designed to supply image information generated by the image generation device to a person wearing the visualization system, and a polarization unit designed to polarize light penetrating the optical system differently in two spatial regions. The invention further relates to a surgical visualization system having such a head-mounted visualization system and to a visualization method for a surgical environment.

18 Claims, 7 Drawing Sheets

Figure 2:
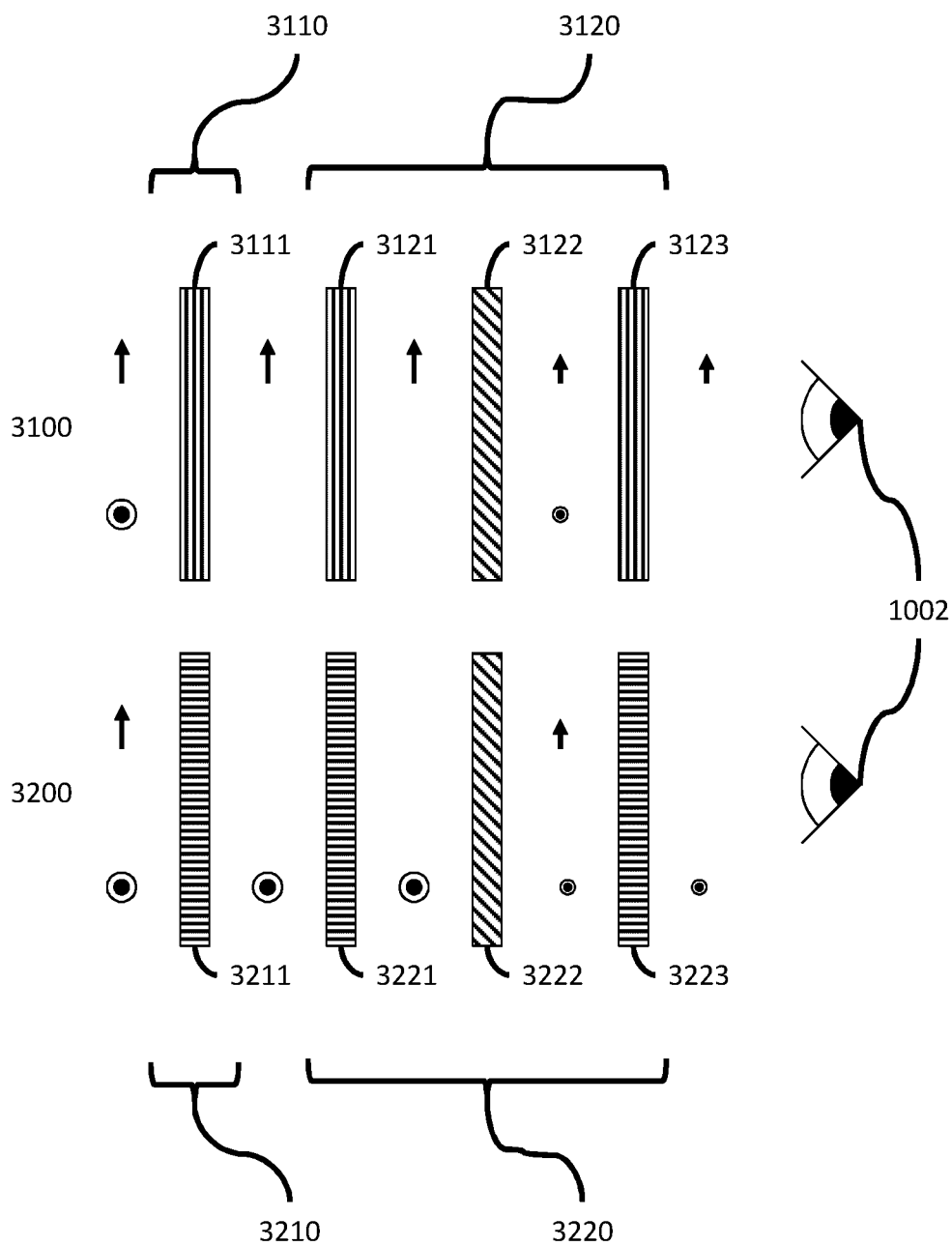

(51) Int. Cl.
  *G02B 5/30* (2006.01)
  *G02B 27/28* (2006.01)
  *G02B 30/25* (2020.01)

(52) U.S. Cl.
  CPC ......... *G02B 27/0179* (2013.01); *G02B 30/25* (2020.01); *A61B 2090/372* (2016.02); *G02B 2027/0118* (2013.01); *G02B 2027/0138* (2013.01); *G02B 2027/0178* (2013.01); *G02B 2027/0187* (2013.01); *G02B 27/283* (2013.01)

(58) Field of Classification Search
  CPC .... G02B 2027/0118; G02B 2027/0138; G02B 2027/0178; G02B 2027/0187; A61B 90/37; A61B 2090/372; A61B 2017/00203; A61B 2017/00216; A61B 2090/371; A61B 2090/502
  USPC ......................................................... 250/225
  See application file for complete search history.

(56) References Cited

U.S. PATENT DOCUMENTS

| | | | |
|---|---|---|---|
| 10,078,236 | B2 | 9/2018 | Hayashi et al. |
| 10,642,040 | B2 | 5/2020 | Mukawa |
| 10,659,772 | B1 * | 5/2020 | Hager ................ G02B 27/0172 |
| 11,150,479 | B2 | 10/2021 | Saur et al. |
| 11,670,054 | B2 | 6/2023 | Coup et al. |
| 2014/0340287 | A1 | 11/2014 | Achilefu et al. |
| 2015/0260995 | A1 | 9/2015 | Mukawa |
| 2016/0034048 | A1 | 2/2016 | Tanaka et al. |
| 2017/0184894 | A1 | 6/2017 | Hayashi et al. |
| 2017/0244958 | A1 | 8/2017 | Shanmugam |
| 2017/0323482 | A1 | 11/2017 | Coup et al. |
| 2018/0089871 | A1 | 3/2018 | Ko et al. |
| 2018/0262743 | A1 | 9/2018 | Casas |
| 2019/0255946 | A1 | 8/2019 | Takahashi |
| 2019/0339528 | A1 | 11/2019 | Freeman et al. |
| 2020/0007857 | A1 | 1/2020 | Kasahara et al. |
| 2020/0268236 | A1 | 8/2020 | Chiba et al. |
| 2023/0088437 | A1 | 3/2023 | Hauger et al. |

FOREIGN PATENT DOCUMENTS

| | | | |
|---|---|---|---|
| CN | 203324583 | U | 12/2013 |
| CN | 106772981 | A | 5/2017 |
| CN | 106918963 | A | 7/2017 |
| CN | 109069935 | A | 12/2018 |
| CN | 110300905 | A | 10/2019 |
| CN | 110770637 | A | 2/2020 |
| DE | 10 2017 123 894 | B3 | 2/2019 |
| DE | 10 2018 215 931 | A1 | 10/2019 |
| JP | H08-286141 | A | 11/1996 |
| JP | 2003250812 | A * | 9/2003 |
| JP | 2017-203952 | A | 11/2017 |
| WO | WO 2001074235 | A1 | 10/2001 |
| WO | WO 2011160200 | A1 | 12/2011 |
| WO | WO 2012/039877 | A1 | 3/2012 |
| WO | WO 2013/175465 | A1 | 11/2013 |
| WO | WO 2015/126466 | A1 | 8/2015 |
| WO | WO 2019/049997 | A1 | 3/2019 |
| WO | WO 2021/175776 | A1 | 9/2021 |

OTHER PUBLICATIONS

Office Action of JP Patent Application No. 2022-552670, mailed Jun. 20, 2023, 8 page(s).
Office Action of German Application No. 10 2020 202 624.6, mailed Jan. 4, 2021.
International Preliminary Report on Patentability, WIPO Application No. PCT/EP2021/054900, mailed Jul. 4, 2022.
Office Action of JP Patent Application No. 2022-552670, mailed Jun. 20, 2023, 5 page(s).
Office Action of JP Patent Application No. 2022-552670, mailed Oct. 24, 2023, 11 page(s).
Office Action of JP Patent Application No. 2022-552647, mailed Oct. 10, 2023, 7 page(s).
Office Action (English Translation) of German Application No. 10 2020 131 029.3, mailed Sep. 1, 2021.
Office Action of German Application No. 10 2020 131 029.3, mailed Sep. 1, 2021.
Office Action (English Translation) of German Application No. 10 2020 202 624.6, mailed Jan. 4, 2021.
PCT International Search Report and Written Opinion of the International Searching Authority, WIPO Application No. PCT/EP2021/054900, mailed Apr. 21, 2021.
PCT International Search Report and Written Opinion of the International Searching Authority, WIPO Application No. PCT/EP2021/055034, mailed May 17, 2021.
Office Action received for Chinese Patent Application No. 202180018244.0, mailed Sep. 2, 2024, (10 pages).
Office Action received for Chinese Patent Application No. 202180018008.9, mailed Sep. 15, 2024, (10 pages).

* cited by examiner

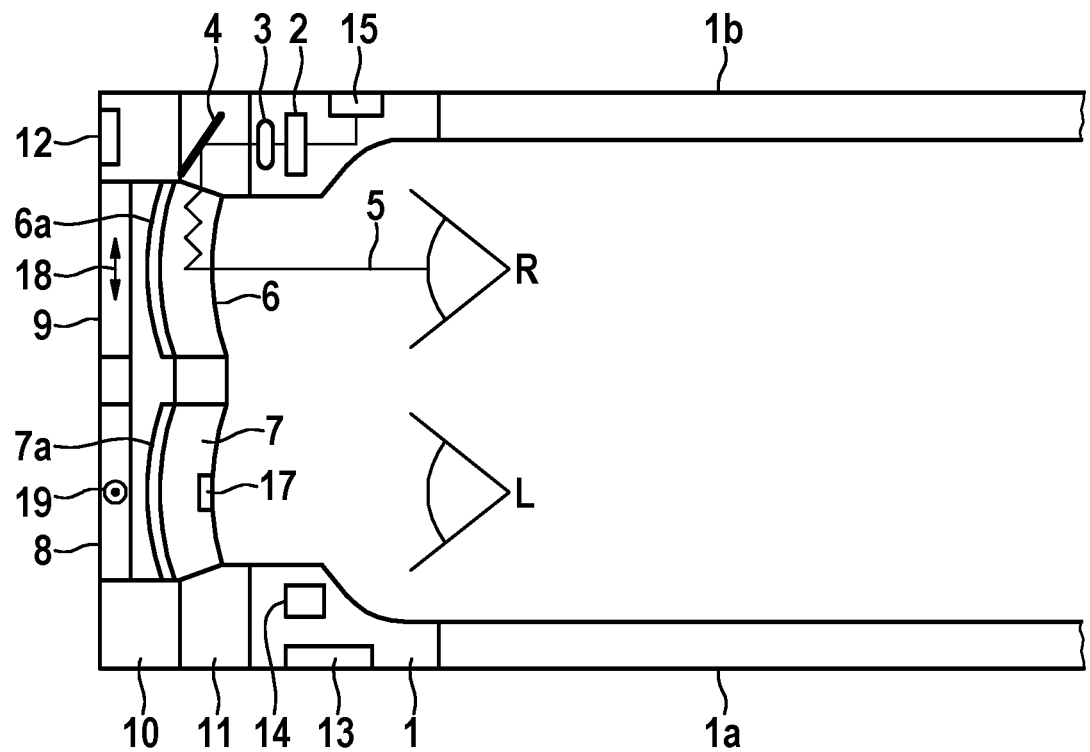
Fig. 1

HEAD-MOUNTED VISUALIZATION SYSTEM

CROSS-REFERENCE TO RELATED APPLICATIONS

The present application is a national phase entry of International Application No. PCT/EP2021/054900, filed Feb. 26, 2021, which claims priority to German Patent Application No. 10 2020 202 624.6, filed Mar. 2, 2020, and German Patent Application No. 10 2020 131 029.3, filed Nov. 24, 2020, which are each incorporated herein by reference in their entirety.

The present invention relates to a head-mounted visualization system, to a surgical visualization system having a head-mounted visualization system, and to methods for visualization in a surgical environment.

In microsurgery, surgical microscopes are used for magnified visualization of the surgical site. In addition to the magnification, the stereoscopic impression is of critical importance for the success of the procedure. Analog surgical microscopes have been meeting these requirements for many years with stereo optics and observation through eyepieces. In addition to observation through the eyepieces, some modern surgical microscopes also offer digital 3D visualization with the aid of stereo monitors.

In addition to stereo monitors, what are known as boom systems and head-mounted displays (HMDs) are considered for the visualization of the stereoscopic video image data. Boom systems are compact digital eyepieces that substantially consist of two microdisplays and two eyepieces and are mounted on a stand. HMDs, by contrast, are head-mounted systems and are available in two variants: VR-HMDs completely mask the real environment and display digital 3D data by means of microdisplays. AR-HMDs, by contrast, enable the view of the real environment and allow the augmentation of digital contents that are presented in a spatially fixed overlay on the real world. A corresponding AR-HMD is available from Magic Leap, for example.

However, there are currently two reasons why HMDs are not yet, or hardly ever, used for microsurgery:

The image quality requirements for what is known as "surgical use case", i.e. the presentation of the image data of the surgical site to the surgeon during the procedure, are very high and are not met by current HMDs. This is due to the fact that HMDs need to be very lightweight and compact, which means that compromises have to be made in terms of image quality. This is also due to the fact that the requirements for high image quality for typical consumer applications are not necessary.

With today's HMDs, the aforementioned surgical use case requires operation that corresponds to a VR mode, because the surgeon must be able to perceive the surgical site in the best possible stereoscopic way. However, numerous applications require the HMD to be operated in an AR mode: For example, at the beginning of the procedure, it is helpful to overlay the site of a craniotomy directly on the patient's skull. An HMD should also enable the surgeon to view the real environment, e.g. to view the sterile table with the instruments. The use cases just mentioned therefore make an HMD that can be switched between an AR and a VR mode appear necessary. None of the currently available HMDs has such technology with an image quality in the VR mode that is even remotely adequate. This is the second reason why no or hardly any HMDs have been used in microsurgery to date.

The present invention is intended to provide a surgical visualization system having a head-mounted visualization system and methods for visualization in a surgical environment using a head-mounted visualization system.

The aforementioned objects are achieved by a surgical visualization system and a method according to the independent claims. Advantageous embodiments are evident from the features of the dependent claims.

An embodiment of a head-mounted visualization system has:
- a wearing system,
- at least one light-transmissive optical system,
- an image generation device that is designed to generate image information based on the image data supplied to the image generation device,
- wherein the optical system is designed to supply image information generated by the image generation device to a person wearing the visualization system, and
- a polarization unit which is designed to polarize light penetrating the optical system differently in two spatial regions.

The present invention is based on the basic idea of using a conventional AR-HMD in combination with a stereo monitor. The polarization unit is therefore adapted so that the user can stereoscopically correctly perceive the image presented on a stereo monitor with the HMD when looking through the optical system of the HMD. For this purpose, the polarization unit can be designed to interact with polarizers of the stereo monitor.

The light-transmissive optical system can be held or holdable on the wearing system or can be arranged on it or be integrated in the wearing system.

The image generation device can be integrated in the wearing system or be held or holdable on the wearing system or be arranged on the wearing system.

Moreover, the optical system can be designed, in the state in which it is held on the wearing system, to supply image information generated by the image generation device that is likewise held on the wearing system or is integrated therein to a person wearing the visualization system.

The polarization unit can be held or holdable on the wearing system or can be arranged on it or be integrated in the wearing system.

In one embodiment, the polarization unit is designed so that it can be removed and held on the wearing system. In this embodiment, the user can use the visualization system without a polarization unit if the light attenuation resulting from the polarization unit disturbs said user.

In a further embodiment, the polarization unit and the light-transmissive optical system are held on the wearing system so that they can be interchanged for one another. In this embodiment, the user can optionally use only the polarization unit if they do not require augmentation information, or use only the optical system if they desire augmentation but do not require stereoscopic perception of the image presented on a stereo monitor. In the third variant, the user can use both the optical system and the polarization unit if they wish to stereoscopically perceive the image presented on the stereo monitor and wish also to receive additional augmentation information.

A further embodiment has a first light-transmissive optical system for a left eye and a second light-transmissive optical system for a right eye. In this embodiment, the polarization unit can have a first polarizer upstream of the first optical system and a second polarizer upstream of the second optical system.

In one embodiment, the polarization unit is designed to polarize light penetrating the optical system in two different surface regions in directions perpendicular to one another.

The mutually perpendicular polarization directions can be, for example, mutually perpendicular linear polarization directions or mutually orthogonal circular polarization directions, i.e. right circular and left circular.

According to another embodiment, the polarization unit comprises a linear polarization filter and a λ/4 plate, wherein the λ/4 plate is arranged upstream of the linear polarization filter in the direction of a first eye of a user, i.e. the λ/4 plate is arranged farther from the eye than the linear polarization filter when the visualization system is worn on the head. Depending on the orientation of the fast axis of the λ/4 plate in relation to the alignment of the subsequent linear polarization filter, the polarization unit can be designed to transmit light with a left-circular polarization or with a right-circular polarization, wherein light, after it has passed through the linear polarization filter, has a linear polarization.

In a further embodiment, the optical transmission of the optical system is switchable or variable in a controlled manner. In particular, the optical transmission of the optical system can be differently variable in different surface regions. In this embodiment, the optical transmission can be adapted to the ambient conditions by switching different surface regions of the optical system to a different optical transmission. For example, it is possible to reduce the optical transmission in field regions in which a user perceives the augmentation information so that the augmentation information is easily perceivable in bright ambient light. On the other hand, it is possible to switch the optical transmission to particularly high in field regions in which a user perceives the stereo display.

Corresponding layers with switchable optical transmission can be implemented for example analogously to an LCD display or as an electrochromic layer that is controllable pixel by pixel.

The optical transmission of the optical system can be switchable or variable in a controlled manner with the aid of a light attenuator. For this purpose, a polarization filter is arranged in the polarization unit and a light attenuator is arranged in the optical system. The light attenuator is arranged here downstream of the polarization filter in a light direction toward the eye. Arranging the light attenuator downstream of the polarizer makes it possible to mask partial regions of the natural field of view without affecting the property of polarizing light that penetrates the optical system required for stereoscopic perception differently in two spatial regions.

The light attenuator can have a controllable liquid crystal layer. The liquid crystal layer can comprise one or more separately controllable liquid crystal pixels or liquid crystal segments. In this way, it can be made possible to influence different points of the liquid crystal layer in their effect on incident light.

The light attenuator may have an output linear polarization filter and an input linear polarization filter. In exemplary embodiments, the input polarization filter of the light attenuator can be identical to the linear polarization filter of the polarization unit. In this way, optical elements of the optical system can be omitted, if necessary. This can make it possible for the head-mounted visualization system to be designed more easily and possibly to be produced more cost-effectively.

The liquid crystal layer can be configured to supply the image information generated by the image generation device to a person wearing the visualization system. For example, liquid crystal pixels can be controlled differently in order to display additional parameters to the user of the head-mounted visualization system.

The head-mounted visualization system may comprise a mirror for supplying the image information generated by the image generation device to a person wearing the visualization system, wherein the mirror is arranged downstream of the light attenuator in the light direction toward the user's first eye, i.e. in a state in which the visualization system is worn on the person's head, the light attenuator is located farther from the eye than the mirror.

It is also conceivable to provide a waveguide in order to supply the image information generated by the image generation device to a person wearing the visualization system, wherein the waveguide is arranged downstream of the light attenuator in the light direction toward the first eye of the user, i.e. when the visualization system is worn on the head of the person, the light attenuator is arranged farther from the eye than the waveguide. As a result, the light attenuator can make it easier to perceive the displayed image information especially in a very bright environment.

The head-mounted visualization system can be suitable in particular for use during a surgical procedure. In particular, the head-mounted visualization system can be designed in such a way that it can be easily disinfected after a surgical procedure. Furthermore, the proposed head-mounted visualization system can be made more lightweight due to the elimination of the need to generate the stereoscopic images in the head-mounted visualization system itself. The head-mounted visualization system can therefore have a lower energy consumption than known head-mounted visualization systems, and longer use during the operation or a more lightweight head-mounted visualization system can thus be provided with the same battery capacity.

One embodiment of a surgical visualization system includes a head-mounted visualization system as described in the present patent application, a surgical microscope or endoscope with an image recording device, and a stereo monitor that is designed for stereoscopically reproducing image information recorded with the image recording device.

The surgical visualization system can have a control device that is designed to supply image data to the image generation device.

In a further embodiment, the head-mounted visualization system has an eye tracker, and the control device is designed to control the image data supplied to the image generation device in dependence on output data from the eye tracker.

In a further embodiment, the head-mounted visualization system has a microphone, and the control device is designed to control the surgical microscope in dependence on acoustic information recorded with the microphone.

In a further embodiment, the head-mounted visualization system has a microphone, and the control device is designed to control the image data supplied to the image generation device in dependence on acoustic information recorded with the microphone.

In a further embodiment, the head-mounted visualization system has a gyroscopic sensor for determining changes in the spatial alignment of the head-mounted visualization system, and the control device is designed to control the surgical microscope in dependence on output data from the gyroscopic sensor.

In a further embodiment, the head-mounted visualization system has a gyroscopic sensor for determining changes in the spatial alignment of the head-mounted visualization system, and the control device is designed to control the image data supplied to the image generation device in dependence on output data from the gyroscopic sensor.

In a further embodiment, the optical transmission of the optical system is switchable differently in different surface regions, and the control device is designed to reduce the optical transmission of the optical system in surface regions in which image information generated by the image generation device is supplied to a person wearing the visualization system.

In a further embodiment, the head-mounted visualization system has a camera, and the control device is designed to determine a position of the stereo monitor relative to a position of the head-mounted visualization system by means of image recognition. In this embodiment, the optical transmission of the optical system can be switchable differently in different surface regions, and the control device can be designed to control the optical transmission of the optical system depending on the position of the stereo monitor relative to the position of the head-mounted visualization system.

A method for visualization in a surgical setting comprises the steps of: presenting an image of an operating region on a stereo monitor, observing the image presented on the stereo monitor through a head-mounted visualization system with polarization filters, and providing additional augmentation information by means of the head-mounted visualization system.

In one embodiment of the visualization method, the head-mounted visualization system generates control data, and the augmentation information and/or image information presented on the stereo monitor and/or movements of a motorized stand and/or functions of a surgical microscope are controlled in dependence on the control data generated by the visualization system.

In one embodiment of the method, the assignment between the sensors of the head-mounted visualization system or the output signals of the sensors and the augmentation information to be provided via the head-mounted visualization system can be configurable by the user.

Figure 3:
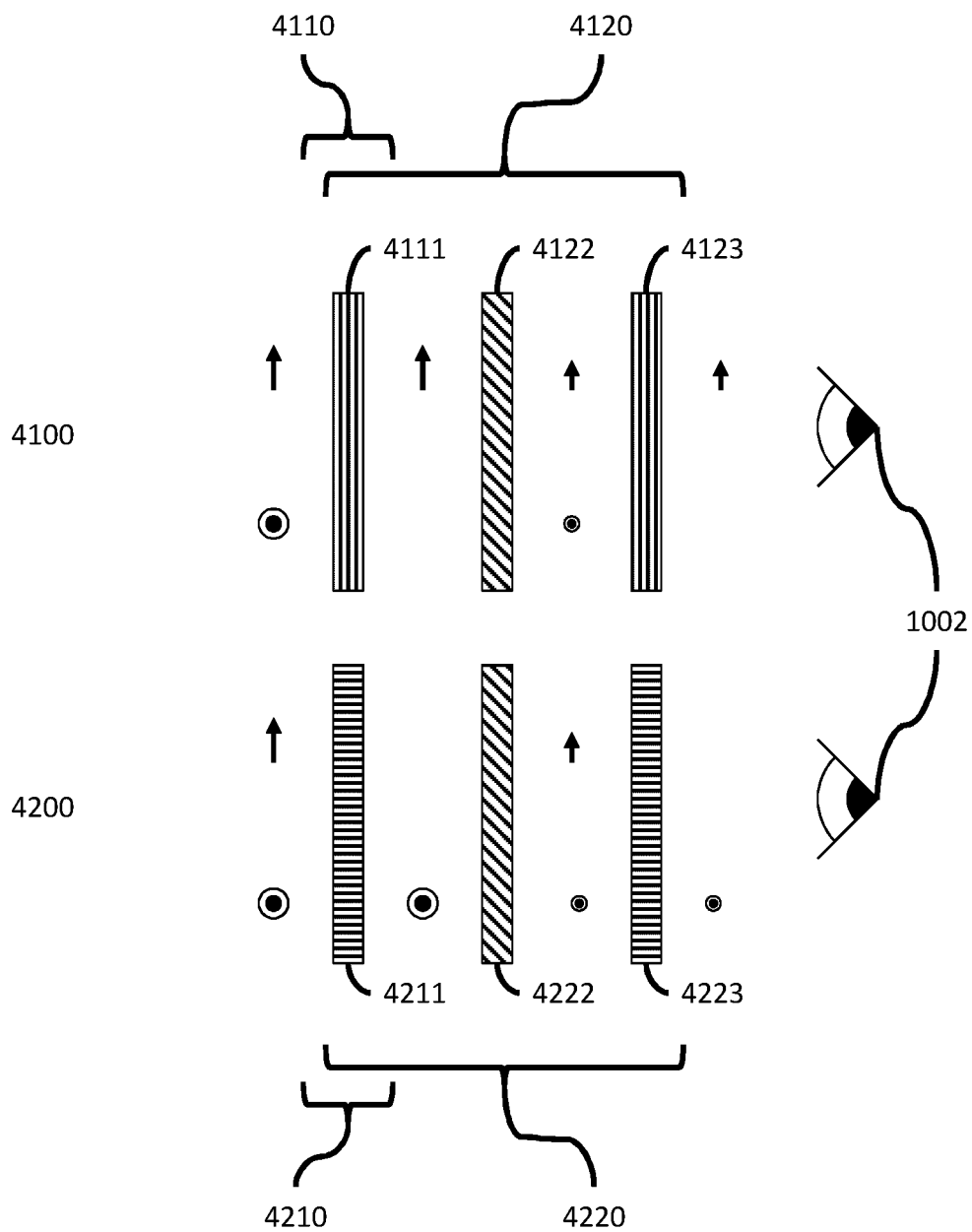
Figure 4:
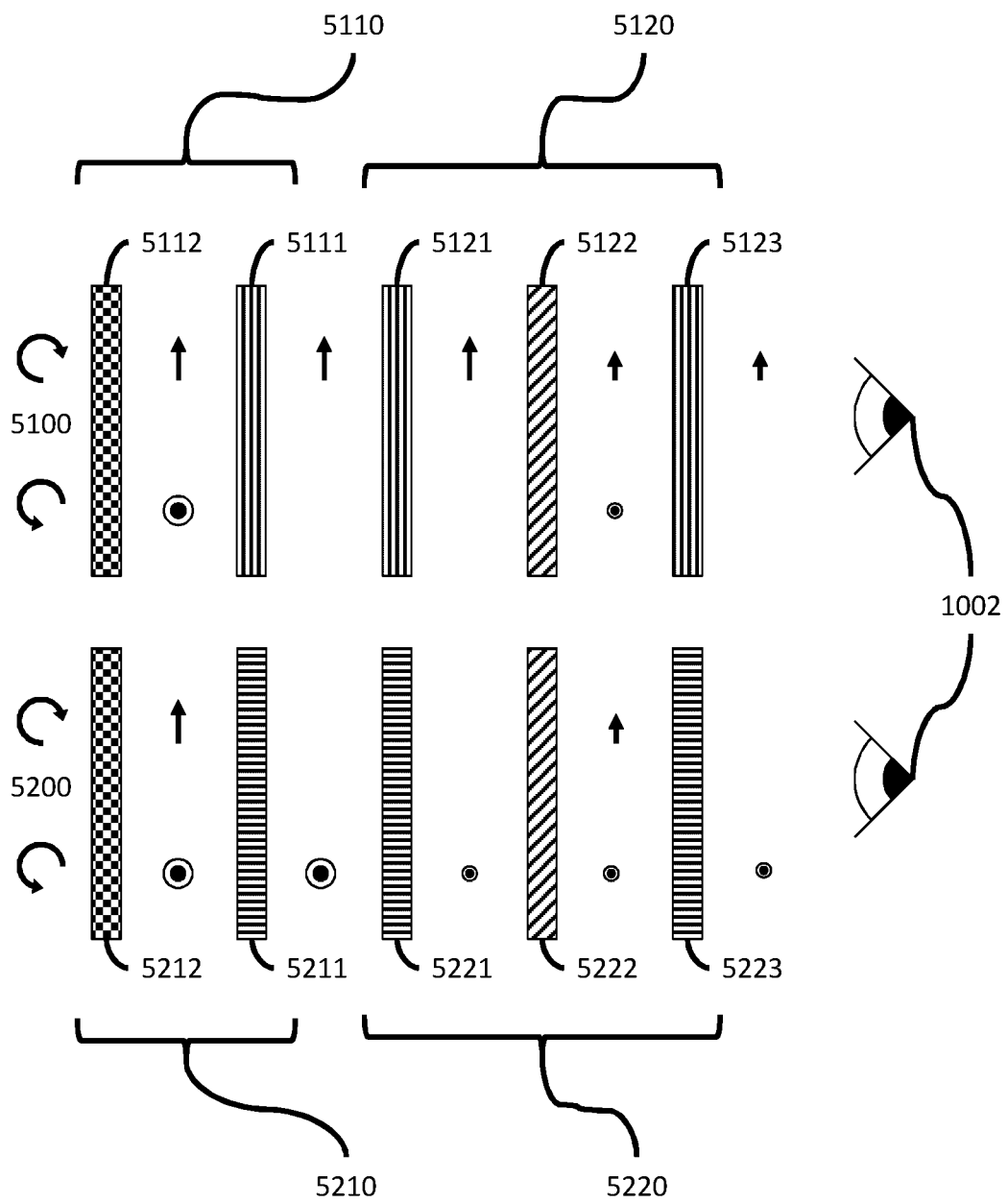
Figure 5:
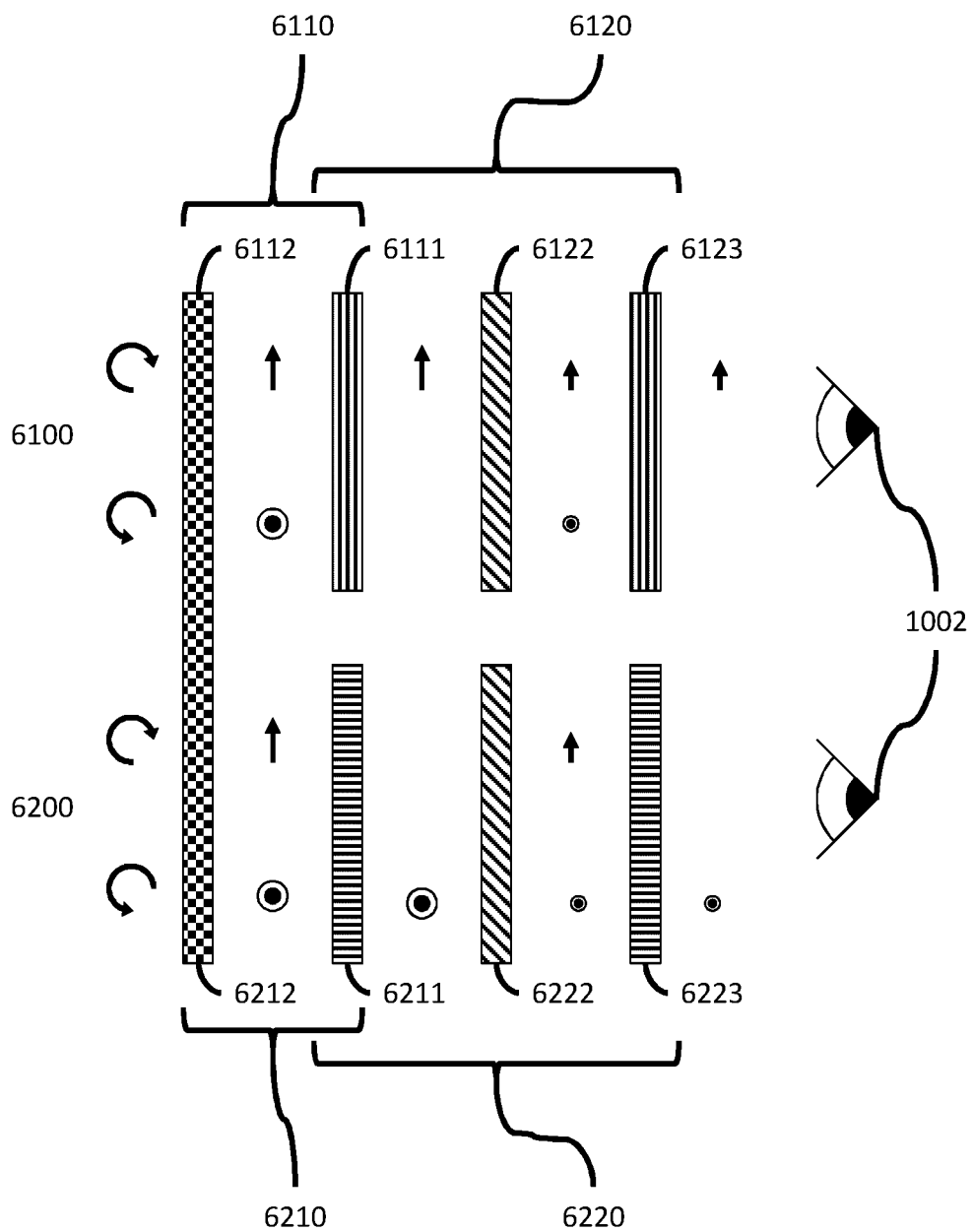
Figure 6:
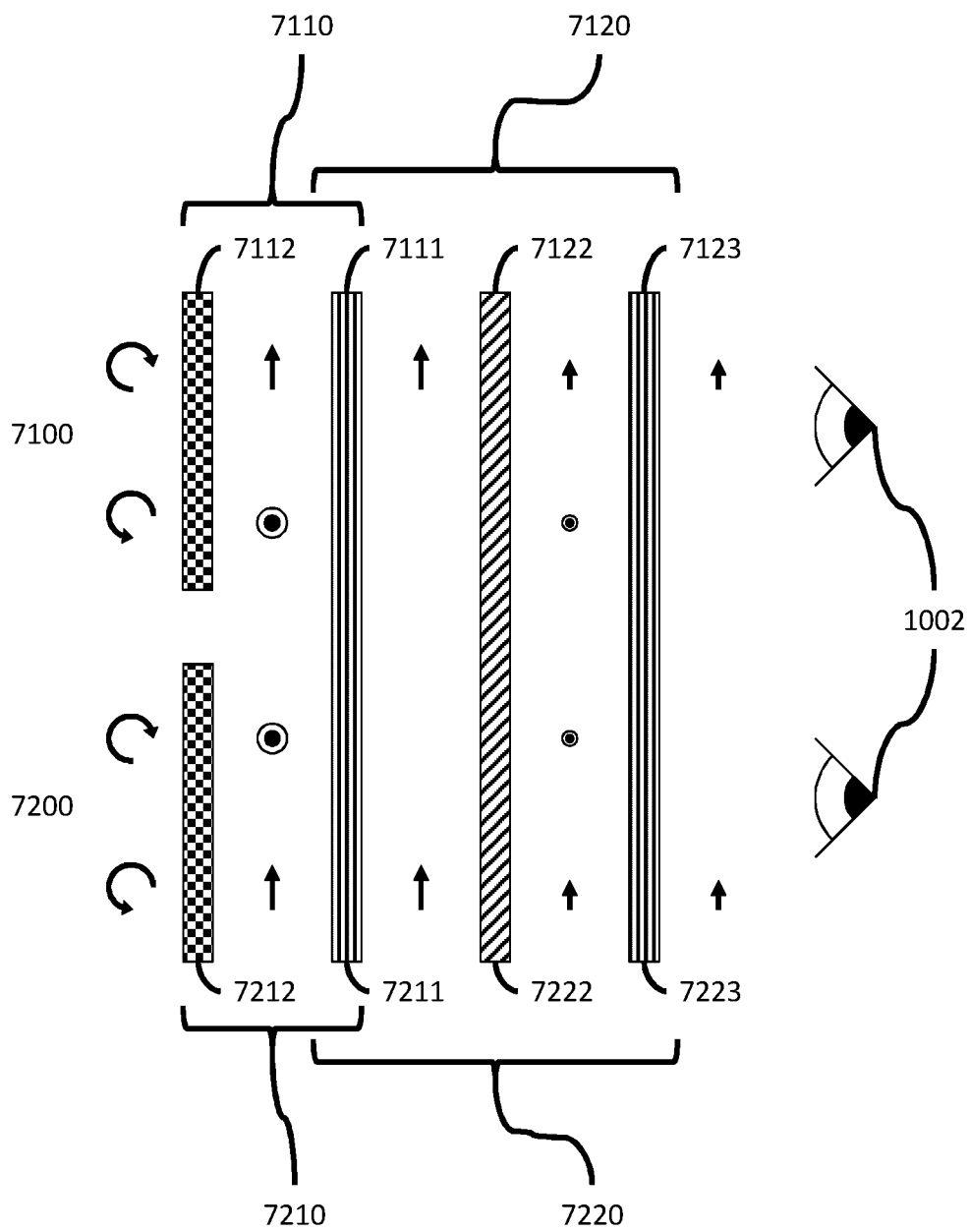
Figure 7:
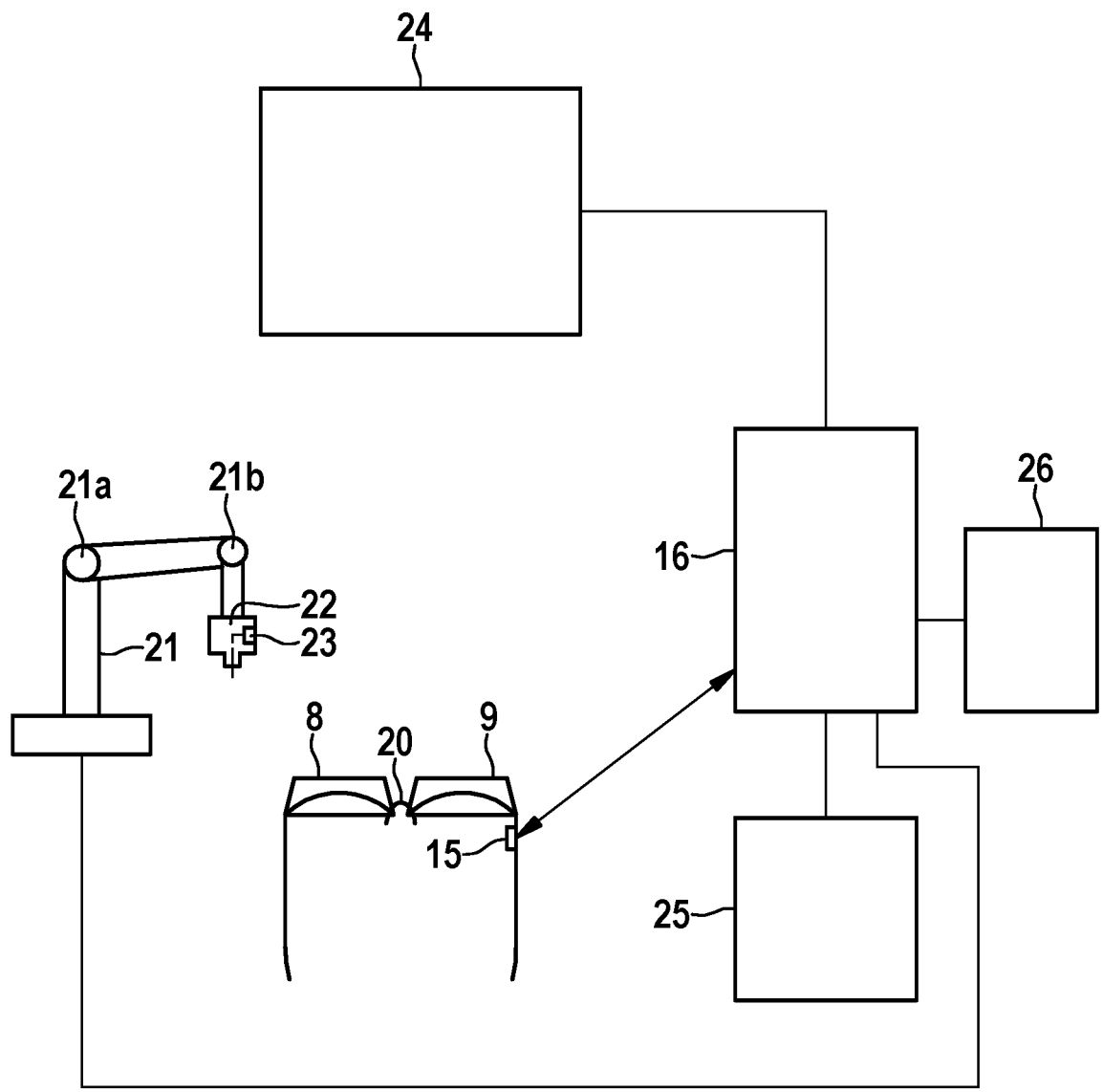

A visualization system and a surgical workstation having a visualization system are explained in more detail below with reference to the figures, in which:

FIG. 1: shows a schematic diagram of an embodiment of a head-mounted visualization system;

FIG. 2: shows a schematic diagram of an embodiment of a polarization unit with a light attenuator for an optical system in a visualization system;

FIG. 3: shows a schematic diagram of a second embodiment of a polarization unit with a light attenuator for an optical system in a visualization system;

FIG. 4: shows a schematic diagram of a third embodiment of a polarization unit with a light attenuator for an optical system in a visualization system;

FIG. 5: shows a schematic diagram of a fourth embodiment of a polarization unit with a light attenuator for an optical system in a visualization system;

FIG. 6: shows a schematic diagram of a fifth embodiment of a polarization unit with a light attenuator for an optical system in a visualization system; and FIG. 7: shows a schematic diagram of a surgical workstation with a visualization system.

The visualization system in FIG. 1 is substantially based on what are known as augmented reality glasses (AR glasses) or what is known as an augmented reality head-mounted display (AR-HMD). The system has a wearing system 1, shown in FIG. 1 as a spectacle frame with a left and a right ear hook 1a, 1b. A module 11 with an optical system 6, 7 is held on the wearing system 1. The optical system 6, 7 is at least partially transparent to light in the visible spectral range.

An image generation device 2, for example in the form of a microdisplay, is integrated in the wearing system 1 or arranged thereon. The image generation device 2 can be controlled and supplied with image data to be presented by a control computer 16 via a wireless interface 15, for example a Bluetooth interface or a WLAN interface. The image information reproduced with the image generation device 2 is directed via a lens 3 and a deflection mirror 4 in the direction of a side surface of the optical system 6, 7. The optical system 6, 7 has internal diffractive structures and what are known as waveguide elements (not shown), which deflects the image information that is generated by the image generation device 2 and coupled into the optical system 6, 7 in the direction (viewing direction axis 5) of an eye R of a head wearing the visualization system and couples it out from the optical system 6, 7.

The optical system 6, 7 has a switchable coating 6a, 7a, with the aid of which the optical transmission of the optical system 6, 7 is switchable. The coating is designed here in such a way that the optical transmission of the optical system is differently settable in different surface regions of the optical system transversely to the viewing direction axis 5. For example, this can reduce the transmission of the optical system 6, 7 in surface regions in which a user sees the image information generated by the image generation device as overlaid on the ambient light passing through the optical system. As a result, the image information generated by the image generation device can also be perceived well in a bright environment.

Furthermore, the visualization system has a further module 10, a polarization unit, with two polarization filters 8, 9. The polarization direction of the ambient light, which is transmitted by one of the polarization filters 8, is polarized perpendicular to the polarization direction of the ambient light, which passes through the other polarization filter. This is indicated by the two arrows 18, 19 in FIG. 1. The polarization directions 18, 19 of the polarization filters are adjusted to the polarization directions of a stereo monitor (not shown in FIG. 1), so that the first polarization filter 8 arranged in front of the left eye L of a user wearing the visualization system only or substantially only transmits the light of the stereo monitor that is intended for the left eye L, and so that the second polarization filter 9 arranged in front of the right eye R of the user wearing the visualization system transmits only or substantially only the light of the stereo monitor that is intended for the right eye R.

The module 11 with the optical system 6, 7 and the module 10 with the polarization filters can be added selectively to the wearing system 1 either alternatively or in combination, with the result that the user has the choice of whether to work only with the polarization filter module 10, only with the module 11 having the optical system 6, 7, or with both modules 10, 11 simultaneously and arranged in series one behind the other.

The wearing system 1 furthermore has a number of further sensors, in particular a forward-facing camera 12, a microphone 13 held on the wearing system or integrated into the wearing system 1, an eye tracker 17, and a gyroscopic sensor 14. Rotational and tilting movements of the wearing system 1 in space can be determined with the gyroscopic sensor 14, and output data characterizing such rotational and tilting movements can be generated. With the eye tracker 17, a movement of the eyes of a user wearing the visualization system can be captured and output data can be generated that characterize this eye movement. The output data generated by the camera 12, the microphone 13, the eye tracker 17, and the gyroscopic sensor 14 can be transmitted to the control computer via the wireless interface 15.

The embodiment shown in FIG. 1 has two optical systems 6, 7, a first of which is assigned to a left eye and a second to a right eye of a user wearing the visualization system. In an alternative embodiment, by contrast, only a single optical system may be present, which covers the visual fields of both eyes of the user wearing the visualization system.

The embodiment shown in FIG. 1 has only a single image generation device 2, and the image information reproduced with the image generation device 2 is presented only to a single eye R. In an alternative embodiment, the image information reproduced with the image generation device 2 can also be presented to both eyes simultaneously. In this case, part of the light generated by the image generation device can be coupled into one optical system 6, and another part of the light generated by the image generation device 2 can be coupled into the other optical system 7. In this case, both optical systems must have integrated diffractive structures and waveguide elements in order to direct light coupled into the optical system to the eye associated with this optical system.

In a further alternative embodiment, two image generation devices can also be provided, one of which couples light it generates into a first of the two optical systems and the other couples the light it generates into the other, second optical system.

FIG. 2 shows elements of a head-mounted visualization system in a higher level of detail. The head-mounted visualization system has a first optical channel 3100, which is assigned to a first eye of a user 1002, and a second optical channel 3200, which is assigned to a second eye of the user 1002. The screen 1003 can present images having a first polarization and a second polarization simultaneously. The first polarization can be, for example, a vertical polarization, as is indicated in FIG. 2 with an arrow pointing up, and a horizontal polarization, as is indicated in FIG. 2 with circles. The head-mounted visualization system has a first polarizer 3110 in the first optical channel 3100 and a first light attenuator 3120 between the first polarizer 3110 and the eye of the user 1002. The first polarizer 3110 comprises a first linear polarization filter 3111, which allows only vertically polarized light to pass. The first light attenuator 3120 has a first input polarization filter 3121 and a first output polarization filter 3123. A first liquid crystal layer 3122, which has a plurality of individually controllable liquid crystal pixels or liquid crystal segments (not shown), is arranged between the first input polarization filter 3121 and the first output polarization filter 3123. The first liquid crystal layer 3122 brings about a rotation of the vertical polarization, with the result that the light passing through the liquid crystal layer has a linear combination of a vertical and a horizontal polarization downstream of the first liquid crystal layer. In this case, the degree of rotation can be changed by appropriately controlling the pixels or segments of the first liquid crystal layer 3122. The first output polarization filter 3123 ensures that only light with vertical polarization is transmitted. Accordingly, the first liquid crystal layer 3122 in combination with the first input polarization filter 3121 and the first output polarization filter 3123 causes light attenuation.

Similarly, the second optical channel 3200 comprises a second polarizer 3210 with a second linear polarization filter 3211 and a second light attenuator 3220 with a second input polarization filter 3221, a second liquid crystal layer 3222, and a second output polarization filter 3223. In contrast to the first channel 3100, the second channel 3200 is transmissive only to light with horizontal polarization. Thus, a channel separation takes place that allows the user of the head-mounted visualization system to stereoscopically perceive the images displayed by the screen 1003.

FIG. 3 shows a further, partially light-transmissive optical system with a first channel 4100 and a second channel 4200. The first channel has a first polarizer 4110 and a first light attenuator 4120 arranged thereafter. The linear polarization filter 4111 of the first polarizer 4110 is therefore identical to an input polarization filter of the first light attenuator 4120, i.e. the linear polarization filter 4111 of the first polarizer 4110 simultaneously forms the input polarization filter of the first light attenuator 4120. The first light attenuator 4120 further has a first liquid crystal layer 4122 and a first output polarization filter 4123.

The first channel 4100 is in turn substantially transmissive to light with vertical polarization. The optical system further has a second channel 4200 with a second polarizer 4210 and a second light attenuator 4220. The linear polarization filter 4211 of the second polarizer 4210 is in turn identical to the input polarization filter of the second light attenuator 4220, i.e. the linear polarization filter 4211 of the second polarizer 4210 simultaneously forms the input polarization filter of the second light attenuator 4220 in the second channel, too. The second light attenuator 4220 additionally has a second liquid crystal layer 4222 and a second output polarization filter 4223. In contrast to the first channel 4100, the second channel 4200 is transmissive substantially only to light with horizontal polarization.

The optical system of FIG. 3 makes it possible to eliminate a linear polarization filter both in the first and in the second channel compared to the optical system of FIG. 2.

FIG. 4 shows a further optical system which is suitable for 3D monitors which generate images with left-circular polarization and right-circular polarization. The use of circular polarizations offers the advantage for the user of the head-mounted visualization system that a clean separation of the images assigned in each case to the left and right channel remains possible even when the head is tilted.

The optical system according to FIG. 4 has a first channel 5100 and a second channel 5200. A first polarizer 5110 and a first light attenuator 5120 are arranged in the first channel 5100. The first polarizer comprises a first linear polarization filter 5111 and a first λ/4 plate 5112. The first linear polarization filter 5111 is arranged between the first λ/4 plate 5112 and the eye of the user 1002 of the head-mounted visualization system. The first polarizer 5110 transmits only light with right-circular polarization, which means that there is vertically polarized light downstream of the polarizer 5110. With the aid of the first input polarizer 5121, the first liquid crystal layer 5122, and the first output polarization filter 5123, the light passing through the first light attenuator 5120 is attenuated.

Similarly, the second channel 5200 has a second polarizer 5210 and a second light attenuator 5220. The second polarizer 5210 comprises a second λ/4 plate 5212 and has a second linear polarization filter 5211 arranged between the second λ/4 plate 5212 and the eye of the user 1002 of the head-mounted visualization system. The second polarizer 5210 has the effect that only left-circular light can pass through the second polarizer 5210 and is present as horizontally polarized light downstream of the second polarizer 5210. The horizontally polarized light is then attenuated by means of the second input polarization filter 5221, the second liquid crystal layer 5222, and the second output polarization filter 5223.

FIG. 5 shows a further example of a head-mounted visualization system, which can be used with circular polarization. The optical system of the head-mounted visualization system again has a first channel 6100 and a second channel 6200.

The first polarizer 6110 of the first channel 6100 and the second polarizer 6210 of the second channel 6200 share a common single λ/4 plate 6112/6122. Furthermore, the input polarization filter of the first light attenuator 6120 is identical to the linear polarization filter 6111 of the first polarizer 6110, and the input polarization filter 6211 of the second light attenuator 6220 is identical to the linear polarization filter 6211 of the second polarizer 6210. Due to the different alignment of the two light attenuators 6120 and 6220 in relation to the fast axis of the λ/4 plate 6112/6212, only right-circular light is allowed through in the first channel 6100 and only left-circular light is allowed through in the second channel 6200.

FIG. 6 shows further details of a head-mounted visualization system.

Similar to FIG. 3, the input polarization filter of the light attenuator 7120 is identical to the linear polarization filter 7111 of the polarizer 7110. The exemplary embodiment according to FIG. 6 has a single input polarization filter 7111 of the light attenuator 7120 common to both channels, which at the same time also forms a single linear polarization filter of the polarizer 7110 common to both channels. The light attenuator 7120 of the first channel 7100 is thus identical to the light attenuator 7220 of the second channel, i.e. the visualization system according to this embodiment has only a single light attenuator common to both channels. Due to a different alignment of the first λ/4 plate 7112 of the first channel and the second λ/4 plate 7212 of the second channel in relation to the linear input polarization filter 7111/7211, light in the first channel 7100 that is incident with right-circular polarization on the first λ/4 plate 7112 is allowed through in the right channel 7100, and light that is incident with left-circular polarization on the second λ/4 plate 7212 is allowed through in the second channel 7200. Accordingly, the optical system according to FIG. 6 also allows channel separation, as a result of which the user of the head-mounted visualization system can stereoscopically perceive the three-dimensional image data displayed by a screen.

A surgical visualization system is shown in FIG. 7. It has a head-mounted visualization device 20 as described above. Furthermore, it has a stand 21 for a surgical microscope 22 or an endoscope (not shown). The stand has motor drives for the articulated connections 21a, 21b. For simplification, only two articulated connections are shown in FIG. 7; such a stand generally has at least six articulated connections with associated drive motors, with the result that a surgical microscope 22 or endoscope held on the stand 21 is freely movable in its six degrees of freedom and can be moved to any point and into any orientation.

The surgical microscope 22 or the endoscope has an image recording device 23, for example in the form of a stereo camera or two individual cameras, with which stereoscopic image information of an operating field can be recorded. The stereoscopic image information recorded with the image recording unit 23 is read by the control computer 16 and passed on by it to a stereo monitor 24. Accordingly, a stereoscopic image of the operating field is presented on the stereo monitor 24. The stereo monitor 24 generates two stereoscopic partial images in this case. The light of the two partial images has different polarizations, with the result that the polarization of a right partial image is perpendicular or orthogonal to the polarization of a left partial image. As an alternative to separating the two stereoscopic partial images with linear polarization, circular polarization can also be used.

A user wearing the head-mounted visualization system 20 can stereoscopically perceive the stereoscopic image reproduced on the stereo monitor 24 the right way round because the polarization directions of the two polarization filters 8, 9 of the head-mounted visualization system 20 are adapted to the polarization directions of the stereo monitor 24. At the same time, the user can also directly observe the operating field or other objects in the environment, such as the sterile table with the instruments, through the optical system and the polarization filters of the head-mounted visualization system 20.

Additional virtual information that would otherwise not be visually accessible to the user can be presented overlaid to the user via the image generation device in the head-mounted visualization system. Such additional information can be information that originates from other devices in the operating room that are not in the user's visual field or that was obtained before the surgery, for example image information from computerized tomography or magnetic resonance images that are stored in a memory 26. However, the additional information can also be information provided by other people during surgery, for example by another expert or pathologist, who has joined remotely from another location via video transmission and to whom the video images recorded with the surgical microscope are made available via video transmission. This expert or pathologist can enter augmentation information on their video monitor, which is then transmitted to the control computer 16 via video back-transmission. The corresponding information is transmitted from the control computer to the head-mounted visualization system 20 via the wireless interface 15.

The sensors in the head-mounted visualization system are used to control the drives 21a, 21b of the stand 21, or other functions of the surgical microscope 22, or the type of information provided by the image generation device in a defined and hands-free manner.

For example, voice control of specific settings on the surgical microscope is possible. Since the microphone of the head-mounted visualization system is always at the same distance from the user's mouth, the acoustic signals recorded with the microphone are not dependent on the position or orientation of the user. Therefore, very stable and reliable voice control can be ensured. Alternatively, it is possible to select the information provided by the image generation device by means of voice control. For this purpose, the acoustic signals recorded with the microphone are transmitted via the interface 15 to the control computer 16 and analyzed by the latter by means of a speech recognition program running on the control computer 16. According to the results of the speech analysis, the associated information is then selected by the control computer 16 and sent to the image generation device via the interface 15, or the motor drives of the stand 21 or motor drives of the surgical microscope 22 are actuated accordingly.

As an alternative or in addition to voice control, movements of the stand 21, motor functions of the surgical microscope 22 or endoscope, or other functions can be controlled via the other sensors, in particular the gyroscopic sensor and/or the eye tracker, of the head-mounted visualization system 20. For this purpose, the output signals from the eye tracker and the gyroscopic sensor are transmitted via the interface 15 to the control computer 16 and evaluated by the latter using a computer program. Depending on the result of the evaluation, the functions of the stand or the surgical microscope assigned to the output signals are then controlled by the computer 16, or the additional information corresponding to the evaluation is selected and sent via the interface 15 to the image generation device.

The assignment between the respective sensor signals and the voice control on the one hand and the function, controlled thereby, of the stand, the surgical microscope, and/or the data respectively provided to the image generation device on the other can be largely freely configurable by the user and assigned in advance by the user as desired. Corresponding user profiles with regard to this assignment can also be stored for several users and called up from a memory at the beginning of a surgery. As an alternative or in addition, corresponding user profiles can also be created for different types of surgical procedures, stored and called up at the beginning of a corresponding procedure.

As already described above, the head-mounted visualization system has a front-facing camera 12. By means of this camera 12, a video stream of the environment permanently or individual images of the environment is/are recorded at specified time intervals and transmitted to the control computer via the interface 15. An image analysis program runs on the control computer, which program is designed in such a way that the respective position of the stereo monitor 24 relative to the head-mounted visualization system is determined in the video stream or in the series of individual images. Based on this image analysis, the control computer generates control data for the switchable coating 6a, 7a, which cause the switchable coating to be switched to maximum optical transmission in the surface regions of the optical systems in which the user perceives the stereo monitor, while the optical transmission in other surface regions, for example in which the user perceives the image provided by the image generation system, is reduced.

The invention claimed is:

1. A surgical visualization system comprising:
    a head-mounted visualization system having a wearing system,
    an image generation device designed to generate image information based on the image data supplied to the image generation device,
        having at least one light-transmissive optical system,
        having a polarization unit which is designed to polarize light penetrating the optical system differently in two spatial regions,
        having a control device; and
    a stereo monitor for stereoscopically reproducing recorded image information,
    wherein the optical system is designed to supply image information generated by the image generation device to a person wearing the head-mounted visualization system, and
    the control device is designed to supply image data to the image generation device,
    wherein the optical transmission of the optical system is switchable differently in different surface regions, and
    wherein the control device is designed
        to determine a position of the stereo monitor relative to a position of the head-mounted visualization system by means of image recognition, and
        to control the optical transmission of the optical system depending on the position of the stereo monitor relative to the position of the head-mounted visualization system in such a manner that the optical transmission is switched to a high optical transmission in the surface regions in which a user of the head-mounted visualization system perceives the stereo monitor, and the optical transmission in other surface regions is reduced.

2. The surgical visualization system as claimed in claim 1, wherein the surgical visualization system furthermore has a surgical microscope or endoscope with an image recording device, and
    wherein the stereo monitor is designed for stereoscopically reproducing image information recorded with the image recording device.

3. The surgical visualization system as claimed in claim 1, wherein the head-mounted visualization system has an eye tracker and the control device is designed to control the image data supplied to the image generation device depending on output data from the eye tracker.

4. The surgical visualization system as claimed in claim 2, wherein the head-mounted visualization system has a microphone and the control device is designed to control the surgical microscope depending on acoustic information recorded with the microphone.

5. The surgical visualization system as claimed in claim 2, wherein the head-mounted visualization system has a microphone and the control device is designed to control the image data supplied to the image generation device depending on acoustic information recorded with the microphone.

6. The surgical visualization system as claimed in claim 1, wherein the head-mounted visualization system has a gyroscopic sensor for determining changes in the spatial alignment of the head-mounted visualization system and the control device is designed to control the surgical microscope or endoscope depending on output data from the gyroscopic sensor.

7. The surgical visualization system as claimed in claim 1, wherein the head-mounted visualization system has a gyroscopic sensor for determining changes in the spatial alignment of the head-mounted visualization system and the control device is designed to control the image data supplied to the image generation device depending on output data from the gyroscopic sensor.

8. The surgical visualization system as claimed in claim 1, wherein the optical transmission of the optical system is switchable differently in different surface regions and wherein the control device is designed to reduce the optical transmission of the optical system in surface regions in which image information generated by the image generation device is supplied to a person wearing the visualization system.

9. The surgical visualization system as claimed in claim 1, wherein the polarization unit is designed to be removable and holdable.

10. The surgical visualization system as claimed in claim 1, wherein the polarization unit and the light-transmissive optical system are held on the wearing system so that they can be interchanged for one another.

11. The surgical visualization system as claimed in claim 1, wherein a first light-transmissive optical system is present for a left eye and a second light-transmissive optical system is present for a right eye.

12. The surgical visualization system as claimed in claim 11, wherein the polarization unit has a first polarizer upstream of the first optical system and has a second polarizer upstream of the second optical system.

13. The surgical visualization system as claimed in claim 1, wherein the polarization unit is designed to polarize light penetrating the optical system in mutually perpendicular directions.

14. The surgical visualization system as claimed in claim 1, wherein the polarization unit is designed to polarize light penetrating the optical system in circularly opposite directions.

15. A method for visualization in a surgical environment, in which
an image of an operating region is presented on a stereo monitor,
the image presented on the stereo monitor is observed through a head-mounted visualization system with polarization filters,
image information is supplied by means of an optical system to a user wearing the head-mounted visualization system,
a position of the stereo monitor relative to a position of the head-mounted visualization system is determined by means of image recognition, and
an optical transmission of the optical system is switched to a high optical transmission in surface regions in which the user perceives the stereo monitor and is reduced in other surface regions, depending on the position of the stereo monitor relative to the position of the head-mounted visualization system.

16. The method as claimed in claim 15, further comprising:
additional augmentation information is provided by means of the head-mounted visualization system,
wherein the head-mounted visualization system generates control data and the augmentation information and/or image information presented on the stereo monitor and/or movements of a motorized stand and/or functions of a surgical microscope are controlled depending on the control data generated by the head-mounted visualization system.

17. The method as claimed in claim 16, further comprising configuring an association between sensors and/or output data from sensors of the head-mounted visualization system and augmentation information to be provided.

18. The method as claimed in claim 16, wherein the augmentation information is transmitted by means of video transmission.

* * * * *